United States Patent [19]
Yokomori et al.

[11] Patent Number: 5,096,835
[45] Date of Patent: Mar. 17, 1992

[54] METHOD OF DISCRIMINATING PARTICLE AGGREGATION PATTERN

[75] Inventors: Yasuhiko Yokomori; Masato Ohta; Masahide Kimura, all of Shizuoka; Kunio Kurata, Chiba; Yoshinobu Kubo, Chiba; Yoshiharu Matsuoka, Chiba, all of Japan

[73] Assignees: Suzuki Jidosha Kogyo Kabushiki Kaisha, Shizouka; Dainabot Co., Ltd., Tokyo, both of Japan

[21] Appl. No.: 520,093

[22] Filed: May 7, 1990

[30] Foreign Application Priority Data

May 17, 1989 [JP] Japan .................. 1-123438

[51] Int. Cl.$^5$ .............. G01N 21/25; G01N 21/59; G01N 33/49
[52] U.S. Cl. .................. 436/165; 436/164; 436/518; 436/805; 73/64.1; 356/39; 356/427; 356/440; 364/555
[58] Field of Search ............ 422/73; 436/34, 518, 436/805, 165, 164; 356/39, 427, 434, 436, 440, 442; 73/64.1; 364/555

[56] References Cited

U.S. PATENT DOCUMENTS 4,563,430  1/1986  Kano et al. .................. 436/164

FOREIGN PATENT DOCUMENTS 0198327  10/1986  European Pat. Off. .
59-132338  7/1984  Japan .
61-215948  9/1986  Japan .
61-59454  12/1986  Japan .

Primary Examiner—David L. Lacey
Assistant Examiner—David Bedding
Attorney, Agent, or Firm—Flynn, Thiel, Boutell & Tanis

[57] ABSTRACT

The aggregation pattern of particles is determined by obtaining luminous intensity curves representative of the particle aggregation pattern, obtaining a first threshold face by cutting the curves with a plane positioned at a first given height, obtaining a second threshold face by cutting the curves with a plane positioned at a second given height and determining the particle aggregation pattern by calculating the ratio of the area of the first threshold face to the area of the second threshold face.

3 Claims, 6 Drawing Sheets

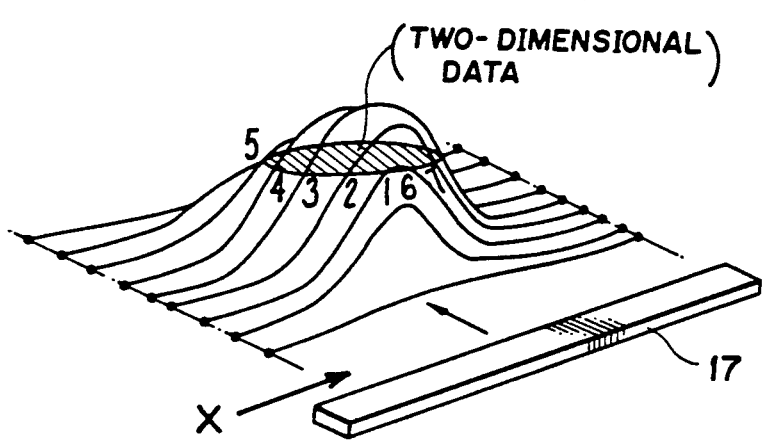
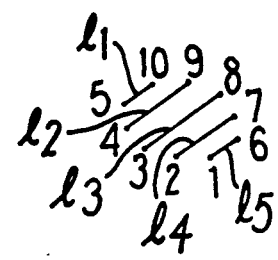
FIG. 7(a) FIG. 7(b)
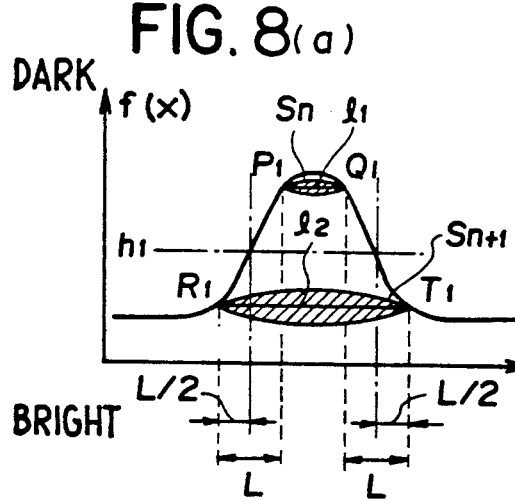
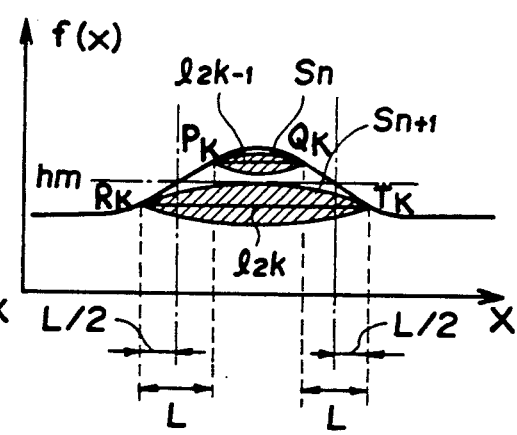
FIG. 8(a) FIG. 8(b)

METHOD OF DISCRIMINATING PARTICLE AGGREGATION PATTERN

The present invention relates to a particle aggregation pattern discriminating method and, more particularly, to a particle aggregation pattern discriminating method suitable for use in the discrimination of various blood types from the aggregation reactive pattern of blood corpuscle particles by what is called a microtiter method, in the clinical laboratory and in the detection of antigen and antibody.

In the medical field, there has widely been used a method whereby aggregation patterns of blood corpuscle particles, latex particles and carbon particles are discriminated and various components (for instance, blood type, various antibodies, various proteins and the like) in the blood, virus, and the like are detected and analyzed. The microtiter method is relatively frequently used as a method of discriminating the aggregation patterns.

In the microtiter method of immunological measurement, there has widely been used a method whereby the presence or absence of aggregation of components on a microplate is detected and a microamount of immune components is measured. In most cases, the presence or absence of aggregation is discriminated by observation by the eyes of the analyzer. In observation discrimination, the presence or absence of aggregation is synthetically discriminated by the human eyes by recognizing a distribution of particles in the well (reactive vessel) as an area whose luminance is a certain degree or less, or by comparing such a distribution with a standard aggregation pattern or a standard nonaggregation pattern, or further by making a continuous stage dilution series of specimen samples, or the like. Therefore, an advanced skill is needed for observation discrimination and such a method is a sensory discriminating method. Therefore, there are inconveniences such that a personal difference occurs due to the person who discriminates and, further, even when the same person discriminates, there is a lack of reproducibility.

Automatization of observation discrimination by an apparatus results in that not only is labor saved, but also the discrimination results are objective and an improvement in measuring accuracy can be expected. Therefore, hitherto, many methods of automatically discriminating particle aggregation patterns have been studied, developed and proposed. For instance, in JP-B-61-59454, there is disclosed a method whereby a one-dimensional photosensitive element is arranged at the center of a concave portion of the bottom surface of a reactive vessel of a microplate and an aggregation image, which is formed on the bottom surface of the reactive vessel, is photoelectrically detected and discriminated. In JP-A-59-132338, there is disclosed a method whereby a number of single photosensitive elements are arranged and the shape of the aggregation image is discriminated. In JP-A-61-215948, there is disclosed a method whereby an aggregation image is picked up by a television camera and the aggregation image is discriminated.

However, in the invention disclosed in JP-B-61-59454, the image is discriminated at one cross-sectional face of the aggregation image. This results in a problem in that the image is discriminated at one cross-sectional face of the aggregation image and if the center of the image deviates from the center of the concave portion of the bottom surface of the reactive vessel or if the whole image is distorted, it is difficult to accurately discriminate. In addition, there is also a problem in that the sensor must be made coincident with the center of the concave portion of the reactive vessel and high mechanical accuracy is required to position both of them.

On the other hand, according to the invention disclosed in JP-A-59-132338, there is the inconvenience of the resolution being bad (1 to 2 mm) due to the limitation in the shape of element and it is difficult to accurately discriminate the aggregation pattern.

Further, according to the invention disclosed in JP-A-61-215948, there is the inconvenience of it being difficult to uniformly discriminate the aggregation images of the reactive vessel in the central and peripheral portions of a microplate. Further, there is also the inconvenience that the amount of data to be processed in each of the reactive vessels is extremely large and takes a great deal of time to discriminate.

It is an object of the present invention to improve the inconveniences of the conventional methods and to provide a particle aggregation pattern discriminating method which can improve the discriminating accuracy and can discriminate at a high speed, particularly, as compared with conventional methods.

Therefore, according to the present invention, there is provided a particle aggregation pattern discriminating method in which there is provided an aggregation reaction checking plate having one or more reactive vessels in which at least a part of a bottom surface is formed as an inclined surface. The bottom surface of each of the reactive vessels is uniformly irradiated by light emitting means arranged on one side of an aggregation reaction checking plate and the transmitted light is received by photosensing means arranged on the other side of the aggregation reaction checking plate through an image forming lens. Particles in a reactive solution enclosed in each of the reactive vessels sediment, and a particle aggregation pattern, formed on the bottom surface, is photoelectrically detected and discriminated, wherein a one-dimensional photosensitive element is used as the photosensing means. By moving the one-dimensional photosensitive element, the transmitted light is continuously received, an image formed on the bottom surface of each of the reactive vessels is retrieved as photosensitive data, an output signal of the one-dimensional photosensitive element is continuously processed, a number of transmitted luminous intensity curves are made, intersection points of a solid which is obtained from a number of transmitted luminous intensity curves and preset threshold faces are obtained. Two points on each of the transmitted luminous intensity curves having a predetermined relationship around each of the intersection points as a center are calculated, first and second pseudo faces are obtained by sequentially connecting those points, and the particle aggregation pattern is discriminated by the area ratio of the first and second pseudo faces. Due to this, the above object of the present invention is accomplished.

BRIEF DESCRIPTION OF THE DRAWINGS

FIGS. 7a and 7b are explanatory diagrams showing a plurality of transmitted luminous intensity curves and examples of the results of the two-dimensional data processes;

FIGS. 8a and 8b are an explanatory diagrams showing a first practical method of an aggregation pattern discriminating method of the present invention;

Embodiments of the present invention will be described hereinbelow on the basis of FIGS. 1 to 11.

Figure 1:
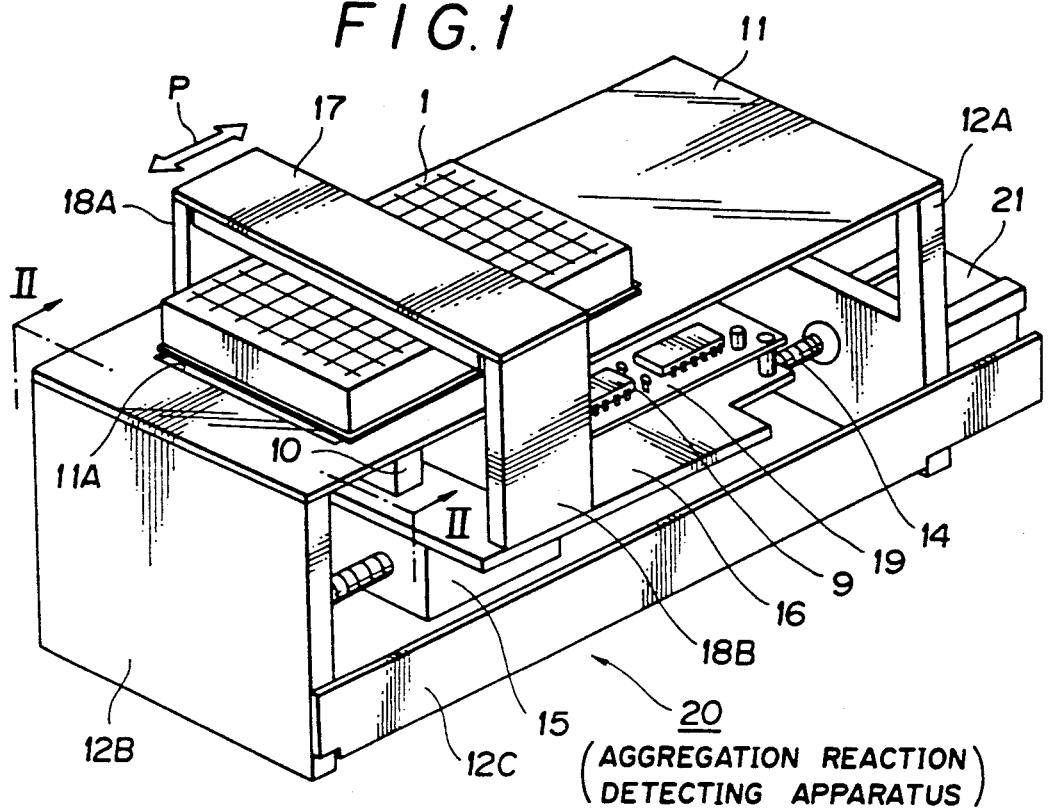
FIG. 1 is a perspective view showing an aggregation reaction detecting apparatus for embodying a particle aggregation pattern discriminating method of the present invention.

FIG. 1 shows an example of an apparatus which embodies a particle aggregation pattern discriminating method according to the present invention.

Figure 3:
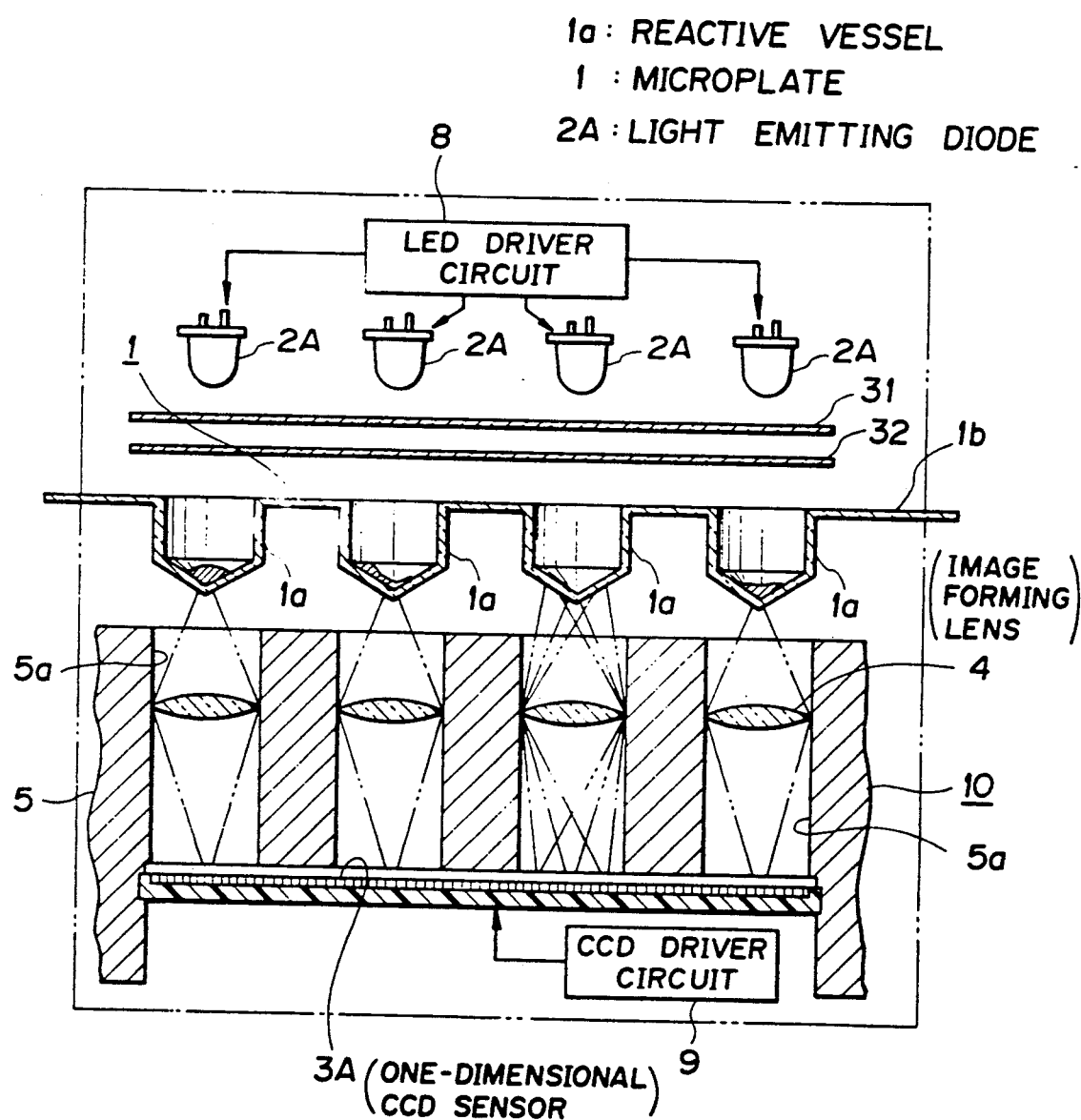
FIG. 3 is an explanatory diagram showing an arrangement of a main section such as light emitting means, photosensing means, and the like in the apparatus of FIG. 1.

An aggregation reaction detecting apparatus 20 shown in FIG. 1 comprises a horizontal plate 11, a supporting member 12A and another supporting member 12B for supporting the horizontal plate 11 at a bottom surface thereof. An opening 11A is formed in a part of the horizontal plate 11. A microplate 1, as an aggregation reaction checking plate, is attached to this opening. As shown in FIG. 3, the microplate 1 comprises a translucent board 1b in which a number of reactive vessels 1a, each of which having its bottom surface formed like a cone, are arranged and formed in a matrix. In this embodiment, as the microplate 1, there is used a microplate in which the reactive vessels 1a are arranged and formed in a matrix of eight rows and twelve columns.

Figure 2:
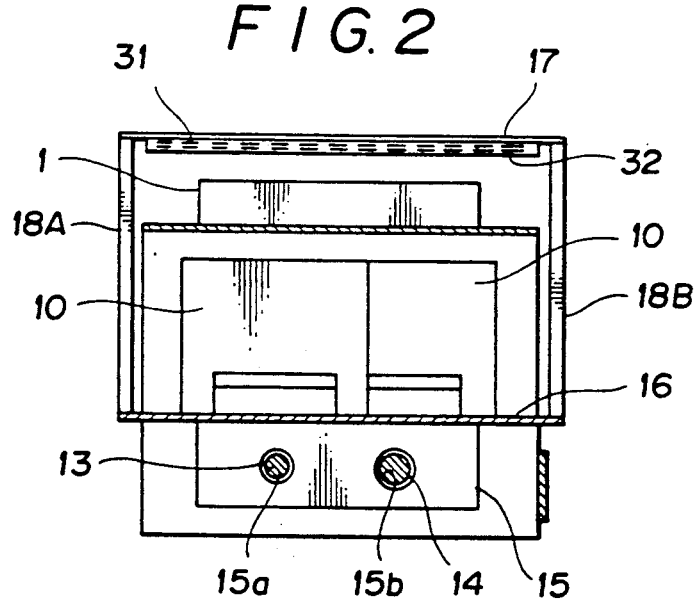
FIG. 2 is a diagram showing a state when it is seen along the line II—II in FIG. 1.

A reinforcing plate 12C, which couples and fixes both supporting members 12A and 12B, is attached therebetween. On the other hand, as shown in FIG. 2, a guide shaft 13 is attached between the supporting members 12A and 12B along the longitudinal direction of the horizontal plate 11. Further, another shaft 14, in which a male screw of a ball screw is formed along the whole length, is arranged between the supporting members 12A and 12B in parallel with the guide shaft 13 and is rotatably installed.

A box 15, shown in FIGS. 1 and 2, is attached to both of the shafts 13 and 14 so that it can reciprocate along both shafts 13 and 14. Practically speaking, a hole 15a having a diameter almost equal to the diameter of shaft 13 and a hole 15b having a diameter almost equal to the diameter of shaft 14 are formed in the box 15. On the other hand, a female screw portion of the ball screw, in which a female screw (not shown) is formed and which faces the foregoing male screw through a ball (not shown), is provided in the box 15.

Figure 4:
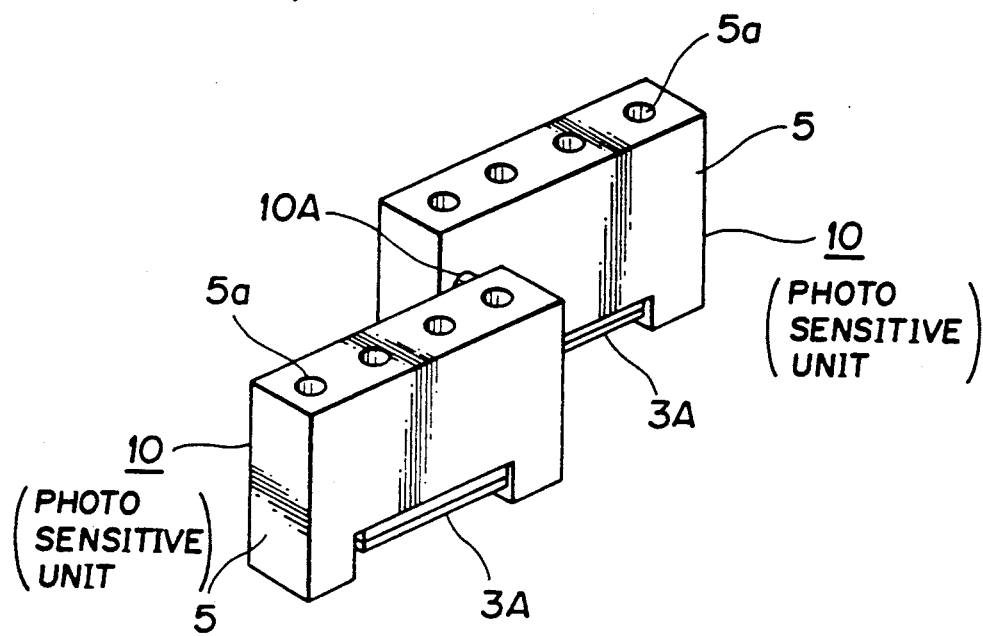
FIG. 4 is an external perspective view showing a photosensitive unit in FIG. 3.

A movable plate 16, on which is mounted a photosensitive unit 10 shown in FIGS. 3 and 4, is arranged and fixed onto the upper surface of the box 15 in parallel with the horizontal plate 11. Supporting plates 18A and 18B for supporting both ends of an upper plate 17, in which light emitting diodes 2A shown in FIG. 3 are fixed to the lower surface thereof, are fixed onto the upper surface of the movable plate 16 so as to perpendicularly cross the movable plate 16. Light diffusing plates 31 and 32 shown in FIG. 3 are integrally held to the lower surface of the upper plate 17. On the other hand, an LED driver circuit 8 for driving light emitting diodes 2A comprising ICs, or the like, is provided under the lower surface of the upper plate 17 (refer to FIG. 3).

A board 19 arranged in parallel with the movable plate 16 is fixed onto the upper surface of the movable plate 16.

A CCD driver circuit 9 for driving a one-dimensional CCD sensor 3A, which comprises an IC or the like and will be explained hereafter, is attached to the board 19.

Further, the two photosensitive units 10, constructed as shown in FIG. 3, are arranged on the upper surface of the movable plate 16 in a manner such that a part in the longitudinal direction of each photosensitive unit 10 mutually overlaps. The photosensitive units 10 are arranged along the vertical columns of the reactive vessels 1a, which are arranged in a matrix on the microplate 1. The photosensitive units 10 are coupled by a coupling member 10A as shown in FIG. 4.

As shown in FIG. 3, the photosensitive unit 10 comprises: a lens holder 5; image forming lenses 4 held to the lens holder 5; and a one-dimensional CCD sensor 3A as a one-dimensional photosensitive element which is attached at the bottom portion of the lens holder 5.

Explanation will be made in further detail. A plurality of holes (in the embodiment, four holes) 5a are formed in the lens holder 5 at intervals equal to the distances among the reactive vessels 1a which are neighboring along the longitudinal direction. Each of the image forming lenses 4 is fixed to a peripheral wall portion of each hole 5a. The one-dimensional CCD sensor 3A is positioned at the bottom portion of the lens holder 5 in parallel with the microplate 1 so as to be spaced downwardly from the image forming lens 4 by a predetermined distance, that is, by almost the same distance as the focal distance of the image forming lens 4.

The photosensitive units 10 are fixed onto the upper surface of the movable plate 16 in such a manner that the four holes 5a formed at intervals equal to the distance between the reactive vessels 1a, which are adjacent in the longitudinal direction, coincide with the reactive vessels 1a.

In FIG. 3, the light emitting diodes 2A, as light emitting means, are arranged above the microplate 1 so as to face the image forming lenses 4. The two light diffusing plates 31 and 32 are arranged between the light emitting diodes 2A and the microplate 1 so as to be in parallel with each other and be spaced from each other by a predetermined interval. The light emitting diodes 2A and the light diffusing plates 31 and 32 are integrally provided on the lower surface side of the upper plate 17 together with the LED driver circuit 8.

A motor 21 for applying a rotational force to shaft 14, through a gear mechanism (not shown), is attached to the outside of the supporting member 12A. Therefore, in the present embodiment, when the motor 21 is driven, the movable plate 16 and upper plate 17 can integrally reciprocate in a manner such that the horizontal plate 11 and microplate 1 are sandwiched at their upper and lower positions and in the direction of arrow P in FIG. 1, that is, along the lateral columns of the reactive vessels la arranged like a matrix on the microplate 1.

The operation of the aggregation reaction detecting apparatus 20 constructed as described above will now be described.

When the motor 21 is driven, the movable plate 16 is put into motion. A positioning means (not shown) is controlled by a CPU (not shown). When the photosensitive units 10 shown in FIG. 2 are moved and set below arbitrary vertical columns of the reactive vessels la formed on the microplate 1, the lights from the light emitting diodes 2A are irradiated onto the microplate 1 through the light diffusing plates 31 and 32. Images of aggregation patterns which are formed on the bottom surfaces of the reactive vessels 1a, located above the photosensitive unit 10, are formed onto the one-dimensional CCD sensors 3A through the image forming lenses 4 by the irradiation lights from the light emitting diodes 2A.

Output signals from the one-dimensional CCD sensors 3A are sent to the CPU (not shown) through A/D converters (not shown). The CPU calculates which reactive vessel is being examined by obtaining a movement amount of the movable plate 16 from a feed amount (rotation amount) of the motor and automatically discriminates the aggregation patterns of the specimens in the reactive vessels as will be explained hereinafter.

Figure 5A:
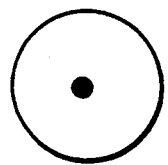
FIGS. 5a and 5b are explanatory diagrams showing typical examples of particle aggregation patterns which are formed on the bottom surfaces of reactive vessels.
Figure 5B:
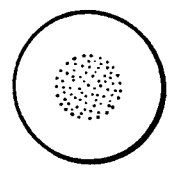

FIGS. 5a and 5b show typical examples of the aggregation pattern on the bottom surface of the reactive vessel 1a. FIG. 5a shows a collection pattern in the case where no aggregation coupling reaction occurs and the sedimented particles roll and drop into the inclined bottom surface of the reactive vessel 1a and are collected near the center. FIG. 5b shows a pattern in the case where the aggregation reaction occurs and the particles are uniformly deposited like a snow over the conical bottom surface of the reactive vessel 1a.

Figure 6A:
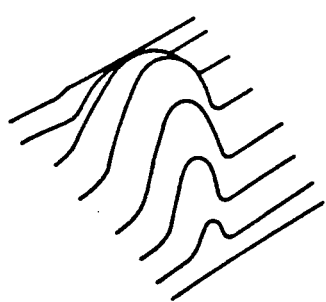
FIGS. 6a and 6b are explanatory diagrams showing transmitted luminous intensity curves which are obtained by processing output signals in the case where the patterns shown in FIGS. 5a and 5b were scanned by a one-dimensional CCD sensor.
Figure 6B:
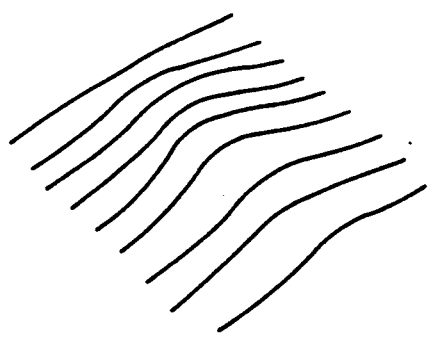

FIG. 6a and 6b show transmitted luminous intensity curves which are obtained by processing the output signal of the one-dimensional CCD sensor 3A when scanning the patterns shown in FIG. 5a and 5b by the CCD sensor 3A. FIG. 6a shows the curve corresponding to the collection pattern of FIG. 5a. FIG. 6b shows the curve corresponding to the uniform deposition pattern of FIG. 5b.

In FIG. 5a, the amount of light transmittance associated with the particles collected near the center of the reactive vessel is relatively low in comparison to the amount of light transmittance associated with the surrounding area where no particles are present (see also FIG. 3). The luminous intensity curves of FIG. 6a exhibit a marked increase in magnitude corresponding to the collected particles of FIG. 5a and the low light transmittance associated therewith. In FIG. 5b, the amount of light transmittance is generally uniform across the bottom surface of the vessel due to the uniformly deposited particles. Thus, the luminous intensity curves of FIG. 6b exhibit a more uniform magnitude than those of FIG. 6a.

An aggregation pattern discriminating method of the present invention will now be described on the basis of FIGS. 7 to 10.

FIGS. 7a and 7b show examples of a plurality of transmitted luminous intensity curves obtained in a manner similar to FIGS. 6a and 6b and the result of the two-dimensional data processes.

The hatched portion in FIG. 7a is a face (threshold face) which is obtained by connecting the points which are obtained by cutting a plurality of transmitted luminous intensity curves at a predetermined threshold level by plane, for instance, at $\frac{2}{3}$ of the maximum height h of the image obtained from each curve. As shown in FIG. 7b, assuming that lengths of portions where the transmitted luminous intensity curves intersect the above face are set to $l_1, l_2, l_3, \ldots$ and $\Delta x$ = sampling interval, from what is called a quadrature by parts, $$S = (l_1 \cdot \Delta x + l_2 \cdot \Delta x + \ldots + l_n \cdot \Delta x)$$

(where, $n \to \infty$)
is nothing but an area of the above face.

As mentioned above, the output of the one-dimensional CCD sensor 3A is converted into two-dimensional data.

FIGS. 8a and 8b are an explanatory diagram showing a first practical method of the aggregation pattern discriminating method of the invention.

It is assumed that a transmitted luminous intensity curve function is $f(x)$.

The first discriminating method is performed according to the following procedure.

1. The transmitted luminous intensity curve function $f(x)$ is scanned.
2. With respect to the transmitted luminous intensity curve functions $f_1(x)$ to $f_n(x)$ obtained by scanning, $$\{[f(x)]_{max} + [f(x)]_{min}\}/2 = h$$

is obtained. The values of h determine the threshold face.

3. The intersection points of the resultant h and the transmitted luminous intensity curve function $f_m(x)$ are set as the center of the check level. Intersection points $P_l$ and $Q_l$ and $R_l$ and $T_l$ on an ordinate axis of the points which are away from the check level center in the direction of an abscissa axis by a predetermined width L and the transmitted luminous intensity curve function, for instance $f_l(X)$, shown in FIG. 8a, are obtained. The length = $l_1$ of line segment $P_lQ_l$ and the length = $l_2$ of line segment $R_lT_l$ are calculated. Similarly, intersection points $P_k$ and $Q_k$ and $R_k$ and $T_k$ with an ordinate axis of the points which are away from a check level center $h_m$ by a predetermined Width L are obtained with respect to each of the transmitted luminous intensity curve functions. A length = $l_{2k-1}$ of the line segment $P_kQ_k$ and a length = $l_{2k}$ ($k = 2, 3, \ldots, n$) of the line segment $R_kT_k$ are calculated.

4. Thereafter, an area $S_n = l_1 + l_3 + \ldots + l_{2n-1}$ of the first pseudo face and an area $S_{n+1} = l_2 + l_4 + \ldots + l_{2n}$ of the second pseudo face are obtained, thereby discriminating the aggregation or nonaggregation by the magnitude of $S_n/S_{n+1}$.

FIG. 8a shows an example of the discrimination of the nonaggregation pattern. FIG. 8b shows an example of the discrimination of the aggregation pattern. The method of FIGS. 8a and 8b is a especially effective method because when there is a distortion of the center or edge of the bottom surface of the reactive vessel of the microplate, the adverse influence of the distortion can be eliminated.

Figures 9A, 9B:
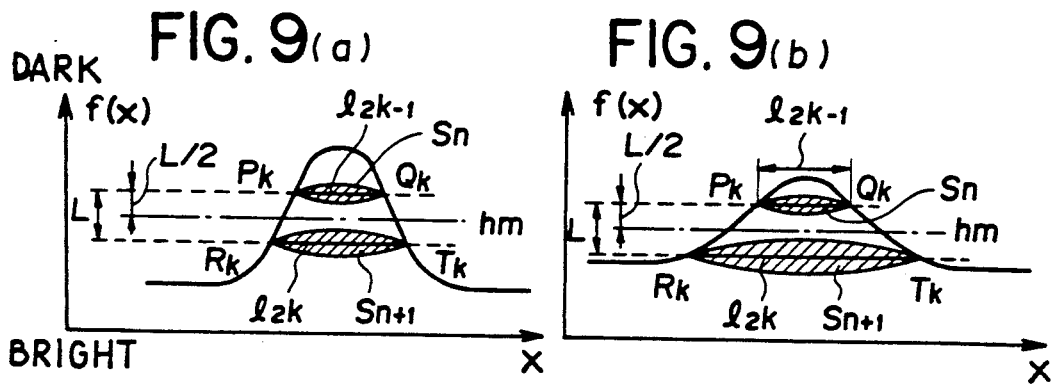
FIGS. 9a and 9b are an explanatory diagrams showing the second practical method of the aggregation pattern discriminating method of the invention.

FIG. 9a and 9b are explanatory diagrams showing the second practical method of an aggregation pattern discriminating method of the invention.

The second discriminating method is executed in the following procedure.

1. The transmitted luminous intensity curve function f(x) is scanned.
2. With respect to the transmitted luminous intensity curve functions $f_1(x)$ to $f_n(x)$ obtained by scanning, $$\{[f(x)]_{max} + [f(x)]_{min}\}/2 = h$$

is obtained.

3. The intersection of the resultant h and a transmitted luminous intensity curve function $f_m(x)$ is set to a check level center. Intersection points $P_k$ and $Q_k$ and $R_k$ and $T_k$ (k = 1, 2, 3, ..., n) on an abscissa axis of the points which are away from the check level center in the direction of an ordinate axis by a predetermined width L and the transmitted luminous intensity curve function are obtained in a manner similar to the above first discriminating method. The line segment $P_kQ_k = l_{2k-1}$ and the line segment $R_kT_k = l_{2k}$ (k = 1, 2, 3, ..., n) are calculated.
4. After that, an area $S_n = l_1 + l_3 + ... l_{2n-1}$ of the first pseudo face and an area $S_{n+1} = l_2 + l_4 + ... + l_{2n}$ of the second pseudo face are obtained, thereby discriminating the aggregation or nonaggregation by the magnitude of $S_n/S_{n+1}$.

FIG. 9a shows an example of the discrimination of the nonaggregation pattern. FIG. 9b shows an example of the discrimination of the aggregation pattern. The method of FIGS. 9a and 9b particularly is effective in the evaluation at a high sensitivity at a predetermined light amount width in the portion of a large change amount of f(x).

Figures 10A, 10B:
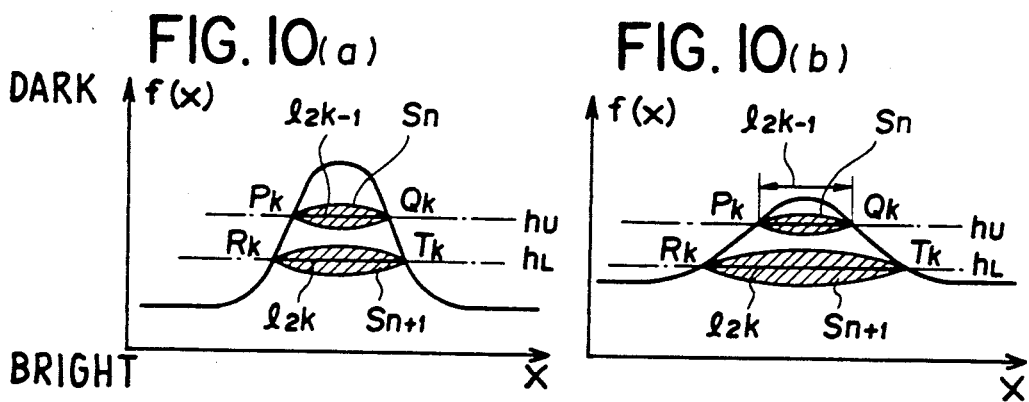
FIGS. 10a and 10b are an explanatory diagrams showing the third practical method of the aggregation pattern discriminating method of the invention.

FIG. 10a and 10b are explanatory diagram showing the third practical method of an aggregation pattern discriminating method of the invention.

The third discriminating method will be executed by the following procedure.

1. The transmitting luminous intensity curve function f(x) is scanned.
2. With respect to the transmitted luminous intensity curve functions $f_1(x)$ to $f_n(x)$ obtained by scanning, the intersection points $P_k$ and $Q_k$ and $R_k$ and $T_k$ (k = 1, 2, 3, ..., n) with first and second threshold faces $h_U$ and $h_L$ which have been preset by a reference aggregation pattern image are obtained as above. The line segment $P_kQ_k = l_{2k-1}$ and the line segment $R_kT_k = l_{2k}$ (k = 1, 2, 3, ..., n) are calculated.
4. After that, $S_n = l_1 + l_3 + ... + l_{2n-1}$ and $S_{n+1} = l_2 + l_4 + ... + l_{2n}$ are obtained. By comparing the magnitude of $S_n/S_{n+1}$ with that of the reference aggregation pattern image, the aggregation or nonaggregation is discriminated.

FIG. 10a shows an example of the discrimination of the nonaggregation pattern. FIG. 10b shows an example of the discrimination of the aggregation pattern. The method of FIGS. 10a and 10b are effective for discrimination at high speed because, particularly, in applications where a reference exists, the processes are simplest.

Figure 11:
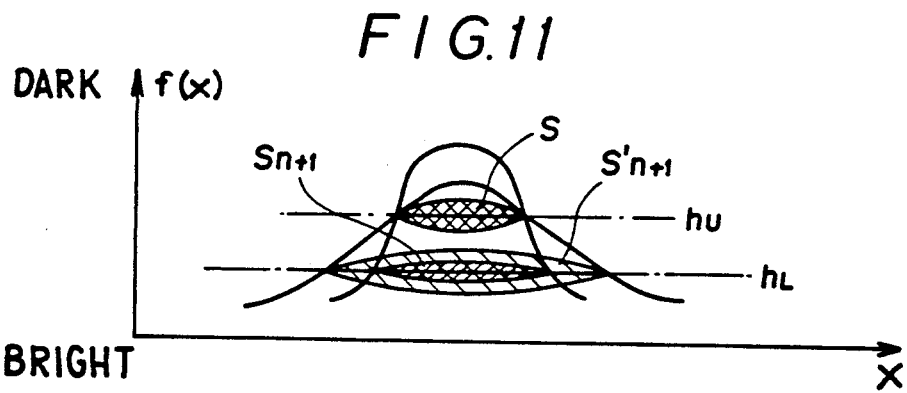
FIG. 11 is an explanatory diagram showing the method under the special conditions of the third method.

FIG. 11 shows the case where in each of the aggregation and nonaggregation patterns of FIGS. 10a and 10b, its cross point is selected to $h_U$. In this case, the discrimination is performed by the magnitude of $S_{n+1}'/S_{n+1}$.

As described above, according to the invention, the one-dimensional photosensitive element is used as a photosensing means, by moving the one-dimensional photosensitive element, the transmitted light is continuously received, an image of which is formed on the bottom surface of each of the reactive vessels and retrieved as photosensitive data, an output signal of the one-dimensional photosensitive element is continuously processed, a number of transmitted luminous intensity curves are made, intersection points of a solid which is obtained from a number of transmitted luminous intensity curves and preset threshold faces are obtained, two points on each of the transmitted luminous intensity curves having a predetermined relation around each of the intersection points as a center are calculated, first and second pseudo faces are obtained by sequentially connecting those points, and an aggregation pattern is three-dimensionally discriminated by a method whereby the particle aggregation pattern is discriminated by the area ratio of the first and second pseudo faces or the like. Therefore, as compared with the method of discriminating by one-dimensional or two-dimensional data, a higher recognizing ratio can be obtained. The resolution can be improved to the resolution (μm level) of the one-dimensional photosensitive element itself. The optimum data can be obtained by merely continuously moving the one-dimensional photosensitive element. Further, it is possible to eliminate the data of the portion which exerts an adverse influence to the measurement due to the distortion of the center or edge of the bottom portion of the reactive vessel. Thus, it is possible to provide an excellent particle aggregation pattern discriminating method in which the measuring accuracy can be remarkably improved and the high speed discrimination can be performed and which is not obtained hitherto.

The embodiments of the invention in which an exclusive property or privilege is claimed are defined as follows:

1. A particle aggregation pattern discriminating method comprising the steps of: providing an aggregation reaction checking plate, said aggregation reaction checking plate comprising at least one reactive vessel having an inclined bottom surface; placing a particle-containing reactive solution in said at least one reactive vessel and allowing the particles to sediment on said reactive vessel bottom surface to form an aggregation pattern; irradiating the bottom surface of said at least one reactive vessel with light from a light emitting means, said light emitting means being positioned above said aggregation reaction checking plate; providing a photosensitive means for receiving said irradiated light from said light emitting means, said photosensitive means being positioned underneath said aggregation reaction checking plate and mounted for translational movement with respect thereto; receiving an image in said photosensitive means of said aggregation pattern, said image being formed by the light passing through the bottom surface of said at least one reactive vessel; producing an output signal from said photosensitive means, said output signal being representative of said image of said aggregation pattern; converting said output signal into a plurality of luminous intensity curves; obtaining a first threshold face, including cutting the luminous intensity curves with a plane positioned at a first given luminous intensity level; obtaining a second threshold face, including cutting the plurality of luminous intensity curves with a plane positioned at a second given luminous intensity level; and determining the particle aggregation pattern, including calculating the ratio of the area of the first threshold face to the area of the second threshold face.

2. A particle aggregation pattern discriminating method, comprising the steps of:

providing at least one reactive vessel having an inclined bottom surface;

placing a particle containing reactive solution in said at least one reactive vessel and allowing the particles to settle on the bottom surface of said at least one reactive vessel to form an aggregation pattern;

directing light downwardly onto the bottom surface of said at least one reactive vessel;

providing a photosensitive means beneath said at least one reactive vessel for receiving said downwardly directed light;

receiving at said photosensitive means a two-dimensional image of said aggregation pattern as formed by the light passing downwardly through the bottom surface of said at least one reactive vessel;

converting said two-dimensional image into a plurality of luminous intensity curves which represent discrete, generally one-dimensional components of said two-dimensional image; and performing an evaluation of said aggregation pattern, including the steps of: defining a first luminous intensity level which intersects each said luminous intensity curve at a pair of first intersection points on said curve, defining a second luminous intensity level which is distinct from said first luminous intensity level and which intersects each said luminous intensity curve at a pair of second intersection points on said curve, calculating for each said luminous intensity curve a first straight-line distance between said first intersection points, calculating for each said luminous intensity curve a second straight-line distance between said second intersection points, obtaining a first sum of all said first straight-line distances, obtaining a second sum of all said second straight-line distances, and dividing said first sum by said second sum.

3. A particle aggregation pattern discriminating method, comprising the steps of:

providing at least one reactive vessel having an inclined bottom surface;

placing a particle containing reactive solution in said at least one reactive vessel and allowing the particles to settle on the bottom surface of said at least one reactive vessel to form an aggregation pattern;

directing light downwardly onto the bottom surface of said at least one reactive vessel;

providing a photosensitive means beneath said at least one reactive vessel for receiving said downwardly directed light;

receiving at said photosensitive means a two-dimensional image of said aggregation pattern as formed by the light passing downwardly through the bottom surface of said at least one reactive vessel;

converting said two-dimensional image into a plurality of luminous intensity curves which represent discrete, generally one-dimensional components of said two-dimensional image; and performing an evaluation of said aggregation pattern, including the steps of: locating a first pair of points on each said luminous intensity curve, locating on each said luminous intensity curve a second pair of points which are distinct from said first pair of points, calculating for each said luminous intensity curve a first straight-line distance between said first pair of points, calculating for each said luminous intensity curve a second straight-line distance between said second pair of points, obtaining a first sum of all said first straight-line distances, obtaining a second sum of all said second straight-line distances, and dividing said first sum by said second sum.

* * * * *

UNITED STATES PATENT AND TRADEMARK OFFICE
CERTIFICATE OF CORRECTION

PATENT NO. : 5 096 835
DATED : March 17, 1992
INVENTOR(S) : Yukinori Harada et al It is certified that error appears in the above-identified patent and that said Letters Patent is hereby corrected as shown below:

ON THE TITLE PAGE:

Item [19] "Yokomori" should be deleted and replaced with --Harada--.

Item [75] "Yukinori Harada" should be added as first inventor.

Signed and Sealed this

Twenty-first Day of September, 1993

Attest:

BRUCE LEHMAN

*Attesting Officer*  *Commissioner of Patents and Trademarks*